United States Patent
Gulian et al.

(10) Patent No.: US 7,785,650 B2
(45) Date of Patent: Aug. 31, 2010

(54) METHOD FOR DIP COATING DOSAGE FORMS

(75) Inventors: Cynthia Gulian, Lansdale, PA (US); Walter G. Gowan, Jr., Westford, MA (US); Kishor B. Parekh, Horsham, PA (US); Joseph M. Morris, Coatesville, PA (US); Thomas J. Markley, North Wales, PA (US); Dennis C. Wieand, Coopersburg, PA (US); Gerard P. McNally, Berwyn, PA (US); Christopher Szymczak, Marlton, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 11/769,028

(22) Filed: Jun. 27, 2007

(65) Prior Publication Data

US 2007/0259098 A1  Nov. 8, 2007

Related U.S. Application Data

(63) Continuation of application No. 10/122,999, filed on Apr. 12, 2002, now abandoned.

(60) Provisional application No. 60/291,127, filed on May 15, 2001, provisional application No. 60/325,726, filed on Sep. 28, 2001.

(51) Int. Cl.
*A61K 9/30* (2006.01)
*A61K 9/34* (2006.01)
*A61K 9/42* (2006.01)
*A61K 9/52* (2006.01)
*B05D 1/18* (2006.01)

(52) U.S. Cl. .............. 427/2.15; 427/2.1; 427/2.16; 427/2.14; 427/430.1; 424/451; 424/460; 424/463; 424/476; 424/479; 424/481

(58) Field of Classification Search .............. 427/2.14, 427/2.21, 430.1, 2.1, 2.15, 2.16
See application file for complete search history.

(56) References Cited

U.S. PATENT DOCUMENTS

| | | |
|---|---|---|
| 1,787,777 A | 1/1931 | Colton |
| 3,185,626 A | 5/1965 | Baker |
| 3,652,294 A | 3/1972 | Marotta et al. |
| 3,751,277 A | 8/1973 | Small et al. |
| 3,802,896 A | 4/1974 | Westall et al. |
| 4,001,211 A | 1/1977 | Sarkar |
| 4,267,164 A | 5/1981 | Yeh et al. |
| 4,313,765 A | 2/1982 | Baird et al. |
| 4,505,890 A | 3/1985 | Jain et al. |
| 4,543,370 A | 9/1985 | Porter et al. |
| 4,572,833 A | 2/1986 | Pedersen et al. |
| 4,576,646 A | 3/1986 | Branco et al. |
| 4,601,894 A | 7/1986 | Hanna et al. |
| 4,643,894 A | 2/1987 | Porter et al. |
| 4,652,313 A | 3/1987 | Den Boer et al. |
| 4,661,162 A | 4/1987 | Kurihara et al. |
| 4,683,256 A | 7/1987 | Porter et al. |
| 4,690,822 A | 9/1987 | Uemura et al. |
| 4,695,467 A | 9/1987 | Uemura et al. |
| 4,695,591 A | 9/1987 | Hanna et al. |
| 4,725,441 A | 2/1988 | Porter et al. |
| 4,775,536 A | 10/1988 | Patell |
| 4,802,924 A | 2/1989 | Woznicki et al. |
| 4,816,259 A | 3/1989 | Matthews et al. |
| 4,820,524 A | 4/1989 | Berta |
| 4,820,529 A | 4/1989 | Uchida et al. |
| 4,828,841 A | 5/1989 | Porter et al. |
| 4,853,230 A | 8/1989 | Lovgren et al. |
| 4,853,249 A | 8/1989 | Takashima et al. |
| 4,880,636 A | 11/1989 | Franz |
| 4,886,669 A | 12/1989 | Ventouras |
| 4,892,742 A | 1/1990 | Shah |
| 4,897,270 A | 1/1990 | Deutsch et al. |
| 4,904,476 A | 2/1990 | Mehta et al. |
| 4,913,893 A | 4/1990 | Varco et al. |
| 4,917,885 A | 4/1990 | Chiba et al. |
| 4,948,622 A | 8/1990 | Kokubo et al. |
| 4,965,089 A | 10/1990 | Sauter et al. |
| 4,981,698 A | 1/1991 | Cherukuri et al. |
| 4,999,189 A | 3/1991 | Kogan et al. |
| 5,009,897 A | 4/1991 | Brinker et al. |
| 5,023,108 A | 6/1991 | Bagaria et al. |
| 5,026,560 A | 6/1991 | Makino et al. |

(Continued)

FOREIGN PATENT DOCUMENTS

EP  0056825 B1  8/1982

(Continued)

OTHER PUBLICATIONS

Light, "Modified Food Starches: Why, What, Where and How", (adapted from Modified Food Starch's Symposium at AACCs 74th Annual Meeting Oct. 29-Nov. 2, 1989).

(Continued)

*Primary Examiner*—Timothy H Meeks
*Assistant Examiner*—Cachet I Sellman

(57) ABSTRACT

Water soluble, gelatin-free dip coatings for pharmaceutical solid dosage forms such as tablets comprising HPMC and xanthan gum, carrageenan, and mixtures thereof, or HPMC and castor oil or maltodextrin.

26 Claims, No Drawings

U.S. PATENT DOCUMENTS

| | | | |
|---|---|---|---|
| 5,059,416 A | 10/1991 | Cherukuri et al. |
| 5,064,650 A | 11/1991 | Lew |
| 5,077,053 A | 12/1991 | Kuncewitch et al. |
| 5,082,669 A | 1/1992 | Shirai et al. |
| 5,098,715 A | 3/1992 | McCabe et al. |
| 5,136,031 A | 8/1992 | Khan et al. |
| 5,146,730 A | 9/1992 | Sadek et al. |
| 5,164,195 A | 11/1992 | Lew |
| 5,186,930 A | 2/1993 | Kogan et al. |
| 5,198,227 A | 3/1993 | Batista et al. |
| 5,209,933 A | 5/1993 | MacFarlane et al. |
| 5,213,738 A | 5/1993 | Hampton et al. |
| 5,228,909 A | 7/1993 | Burdick et al. |
| 5,228,916 A | 7/1993 | Berta |
| 5,248,516 A | 9/1993 | Wheatley et al. |
| 5,252,339 A | 10/1993 | Cristofori et al. |
| 5,270,071 A | 12/1993 | Sharp et al. |
| 5,286,502 A | 2/1994 | Meyers |
| 5,296,233 A | 3/1994 | Batista et al. |
| 5,382,435 A | 1/1995 | Geary et al. |
| 5,393,333 A | 2/1995 | Trouve |
| 5,409,711 A | 4/1995 | Mapelli et al. |
| 5,411,746 A | 5/1995 | Signorino et al. |
| 5,415,871 A | 5/1995 | Pankhania et al. |
| 5,422,121 A | 6/1995 | Lehmann et al. |
| 5,425,950 A | 6/1995 | Danidiker et al. |
| 5,433,960 A | 7/1995 | Meyers |
| 5,436,026 A | 7/1995 | Berta |
| 5,445,829 A | 8/1995 | Paradissis et al. |
| 5,447,726 A | 9/1995 | Nomura |
| 5,459,983 A | 10/1995 | Sadek et al. |
| 5,464,633 A | 11/1995 | Conte et al. |
| 5,470,581 A | 11/1995 | Grillo et al. |
| 5,472,712 A * | 12/1995 | Oshlack et al. ............ 424/480 |
| 5,474,786 A | 12/1995 | Kotwal et al. |
| 5,480,479 A | 1/1996 | Signorino |
| 5,482,718 A | 1/1996 | Shah et al. |
| 5,496,561 A | 3/1996 | Okada et al. |
| 5,498,709 A | 3/1996 | Navia et al. |
| 5,506,248 A | 4/1996 | Nikfar et al. |
| 5,512,314 A * | 4/1996 | Signorino et al. .......... 427/2.14 |
| 5,514,384 A | 5/1996 | Signorino |
| 5,525,354 A | 6/1996 | Posti et al. |
| 5,534,263 A | 7/1996 | Wong et al. |
| 5,538,125 A | 7/1996 | Berta |
| 5,560,926 A | 10/1996 | Franz et al. |
| 5,571,533 A | 11/1996 | Santus et al. |
| 5,591,455 A | 1/1997 | Signorino et al. |
| 5,593,694 A | 1/1997 | Hayashida et al. |
| 5,595,592 A | 1/1997 | Signorino et al. |
| 5,614,218 A | 3/1997 | Olsson et al. |
| 5,622,721 A | 4/1997 | Dansereau et al. |
| 5,630,871 A | 5/1997 | Jordan |
| 5,633,015 A | 5/1997 | Gilis et al. |
| 5,635,208 A | 6/1997 | Parekh et al. |
| 5,641,513 A | 6/1997 | Lech et al. |
| 5,641,536 A | 6/1997 | Lech et al. |
| 5,650,169 A | 7/1997 | Conte et al. |
| 5,658,589 A | 8/1997 | Parekh et al. |
| 5,667,573 A | 9/1997 | Kondou |
| 5,667,802 A | 9/1997 | Grimberg |
| 5,679,406 A | 10/1997 | Berta |
| 5,681,584 A | 10/1997 | Savastano et al. |
| 5,681,585 A | 10/1997 | Oshlack et al. |
| 5,681,684 A | 10/1997 | Kinashi et al. |
| 5,685,589 A | 11/1997 | Kikuchi et al. |
| 5,690,960 A | 11/1997 | Bengtsson et al. |
| 5,698,220 A | 12/1997 | Cardinal et al. |
| 5,707,648 A | 1/1998 | Yiv |
| 5,712,310 A | 1/1998 | Koch |
| 5,725,880 A | 3/1998 | Hirakawa et al. |
| 5,733,575 A | 3/1998 | Mehra et al. |
| 5,738,874 A | 4/1998 | Conte et al. |
| 5,750,148 A | 5/1998 | Maruyama et al. |
| 5,756,123 A * | 5/1998 | Yamamoto et al. .......... 424/451 |
| 5,770,225 A | 6/1998 | Parekh et al. |
| 5,776,479 A | 7/1998 | Pallos et al. |
| 5,792,473 A | 8/1998 | Gergely et al. |
| 5,800,836 A | 9/1998 | Morella et al. |
| 5,807,580 A | 9/1998 | Luber |
| 5,814,336 A | 9/1998 | Kelm et al. |
| 5,814,339 A | 9/1998 | Prudhoc |
| 5,830,503 A | 11/1998 | Chen |
| 5,843,479 A | 12/1998 | Kelm et al. |
| 5,863,559 A | 1/1999 | Phillips et al. |
| 5,885,617 A | 3/1999 | Jordan |
| 5,891,474 A | 4/1999 | Busetti et al. |
| 5,908,638 A | 6/1999 | Huber et al. |
| 5,914,132 A | 6/1999 | Kelm et al. |
| 5,919,485 A | 7/1999 | Cochran et al. |
| 5,922,352 A | 7/1999 | Chen et al. |
| 5,935,602 A | 8/1999 | Dansereau et al. |
| 5,945,124 A | 8/1999 | Sachs et al. |
| 5,968,551 A | 10/1999 | Oshlack et al. |
| 6,022,564 A | 2/2000 | Takechi et al. |
| 6,039,976 A | 3/2000 | Mehra et al. |
| 6,051,255 A | 4/2000 | Conley et al. |
| 6,066,336 A | 5/2000 | Ullah et al. |
| 6,068,856 A | 5/2000 | Sachs et al. |
| 6,077,533 A | 6/2000 | Oshlack et al. |
| 6,077,541 A | 6/2000 | Chen et al. |
| 6,080,426 A | 6/2000 | Amey et al. |
| 6,083,430 A | 7/2000 | Fuisz et al. |
| 6,096,340 A | 8/2000 | Chen et al. |
| 6,113,945 A | 9/2000 | Jacobs et al. |
| 6,120,801 A | 9/2000 | Parekh et al. |
| 6,120,802 A | 9/2000 | Breitenbach et al. |
| 6,123,964 A | 9/2000 | Asgharnejad et al. |
| 6,129,933 A | 10/2000 | Oshlack et al. |
| 6,156,343 A | 12/2000 | Morita et al. |
| 6,165,513 A | 12/2000 | Dansereau et al. |
| 6,183,808 B1 | 2/2001 | Grillo et al. |
| 6,190,692 B1 | 2/2001 | Busetti et al. |
| 6,210,714 B1 | 4/2001 | Oshlack et al. |
| 6,214,376 B1 | 4/2001 | Gennadios |
| 6,214,378 B1 | 4/2001 | Tanida et al. |
| 6,214,380 B1 | 4/2001 | Parekh et al. |
| 6,228,400 B1 | 5/2001 | Lee et al. |
| 6,238,704 B1 | 5/2001 | Suzuki et al. |
| 6,245,350 B1 | 6/2001 | Amey et al. |
| 6,245,356 B1 | 6/2001 | Baichwal |
| 6,248,363 B1 | 6/2001 | Patel et al. |
| 6,270,804 B1 | 8/2001 | Getz et al. |
| 6,274,162 B1 | 8/2001 | Steffenino et al. |
| 6,274,173 B1 | 8/2001 | Sachs et al. |
| 6,294,200 B1 | 9/2001 | Conte et al. |
| 6,309,666 B1 | 10/2001 | Hatano et al. |
| 6,309,668 B1 | 10/2001 | Bastin et al. |
| 6,340,473 B1 | 1/2002 | Tanner et al. |
| 6,348,090 B1 | 2/2002 | Grillo et al. |
| 6,420,473 B1 | 7/2002 | Chittamuru et al. |
| 6,488,962 B1 * | 12/2002 | Berner et al. ............... 424/484 |
| 6,521,257 B1 | 2/2003 | Taniguchi et al. |
| 6,579,545 B2 | 6/2003 | Zyck et al. |
| 6,635,275 B1 * | 10/2003 | Scott et al. .................. 424/451 |
| 6,635,282 B1 | 10/2003 | Flanagan et al. |
| 7,429,619 B2 | 9/2008 | Kamath |

| | | | |
|---|---|---|---|
| 2001/0000471 A1 | 4/2001 | Shen et al. | |
| 2001/0036476 A1 | 11/2001 | Oshlack et al. | |
| 2001/0046511 A1 | 11/2001 | Zerbe et al. | |

FOREIGN PATENT DOCUMENTS

| | | |
|---|---|---|
| EP | 246693 B1 | 11/1987 |
| EP | 0470872 B1 | 2/1992 |
| EP | 0575179 A | 12/1993 |
| EP | 0638310 A | 2/1995 |
| EP | 0 684 301 A2 | 11/1995 |
| EP | 0 717 992 A2 | 6/1996 |
| EP | 0714656 | 6/1996 |
| EP | 0714656 A | 6/1996 |
| EP | 0 733 367 A | 9/1996 |
| EP | 0839527 A | 5/1998 |
| EP | 974344 A2 | 1/2000 |
| EP | 1112738 | 4/2001 |
| EP | 1117736 | 7/2001 |
| EP | 0 934 734 B1 | 10/2002 |
| FR | 2 783 832 A | 3/2000 |
| GB | 1543167 | 3/1979 |
| JP | 63062535 A | 3/1988 |
| JP | 1067645 | 3/1989 |
| JP | 2-48521 | 2/1990 |
| JP | 3279325 | 12/1991 |
| JP | 8-99875 | 4/1996 |
| JP | 7-501073 | 4/1997 |
| JP | 10066556 A | 3/1998 |
| JP | 11180864 | 7/1999 |
| WO | WO 9007859 A | 7/1990 |
| WO | WO 9115548 A | 10/1991 |
| WO | WO 93/09785 A | 5/1993 |
| WO | WO 95/03063 A | 2/1995 |
| WO | WO 95/23594 A1 | 9/1995 |
| WO | WO 98/27151 | 6/1998 |
| WO | WO 98/30341 A | 7/1998 |
| WO | WO 99/03449 A | 1/1999 |
| WO | WO 99/46329 A1 | 9/1999 |
| WO | WO 99/51210 A1 | 10/1999 |
| WO | WO 00/18835 A | 4/2000 |
| WO | WO 00/18835 A1 | 4/2000 |
| WO | WO 00/32174 A2 | 6/2000 |
| WO | WO 00/42998 A1 | 7/2000 |
| WO | WO 00/45794 A1 | 8/2000 |
| WO | WO 00/48574 A1 | 8/2000 |
| WO | WO 01/03677 A | 1/2001 |
| WO | WO 01/07507 A1 | 2/2001 |
| WO | WO 01/26633 A1 | 4/2001 |
| WO | WO 01/26634 A | 4/2001 |
| WO | WO 01/37816 A | 5/2001 |
| WO | WO 01/91721 A2 | 12/2001 |

OTHER PUBLICATIONS

Fegley, "The Effect of Table Shape on the Perception of High Gloss Coating Systems", 2002 Colocon.
European Search Report for EP 02 25 3341 dated Mar. 21, 2003.
European Search Report for EP 02 25 3342 dated Mar. 19, 2003.
European Search Report for EP 02 25 3340 dated Nov. 3, 2004.
Remington: "The Science & Practice of Pharmacy", pp. 208-209 (2000).
Remington: "The Science & Practice of Pharmacy", pp. 1625-1630 (17$^{th}$ Ed.) (1985).
Tricor Systems WGloss 3.4 Model 805A/806H Surface Analysis System Reference Manual (1996).
"Purity® Gum 59" Technical Services Bulletin, 1993.
Zallie, "The Role and Function of Specialty Starches in the Confection Industry" Brochure, pp. 1-16 (1997).
Zallie, "New Starches for Gelling and Non-gelling Applications" reprinted from Manufacturing Confectioner (Nov. 1988).
FMC Biopolymer Brochure, "Carragenan", available at www.fmcbiopolymer.com on Apr. 3, 2001.
Polyvinylpyrrolidone for the Pharmaceutical Industry, Brochure by BASF, pp. 15 and 107-108 (Aug. 1993).
Specifications and Test Methods for EUDRAGIT®, pp. 1-3 (1996).
Applicability of the Monograh . . . EUDRAGIT® S30D, pp. 1 (1994).
Gulian, Frank et al., "Color and Gloss Uniformity of Tablets Coated in a Side-Vented Pan Using Opaglos® 2"; Poster Reprint, American Association of Pharmaceutical Scientists, pp. 1-5, Oct. 2001.
U.S. Appl. No. 10/122,498, filed Apr. 15, 2002.
U.S. Appl. No. 10/122,531, filed Apr. 15, 2002.
U.S. Appl. No. 10/122,999, filed Apr. 12, 2002.
U.S. Appl. No. 10/176,832, filed Jun. 21, 2002.
U.S. Appl. No. 60/325,726, filed Sep. 28, 2001.
U.S. Appl. No. 60/291,127, filed Nov. 15, 2001.
U.S. Appl. No. 10/211,139, filed Aug. 2, 2002.
U.S. Appl. No. 11/769,028, filed Jun. 27, 2007.
U.S. Appl. No. 12/335,069, filed Dec. 15, 2008.
European Search Report for EP 03254789 dated Nov. 18, 2003.
European Search Report for EP 02256752 dated May 28, 2003.
EP Search Report dated Apr. 20, 2007 for EP Application No. 06 07 7180.
Pharmacia Remington, Preformulacion, pp. 2241-2242, publication date prior to May 15, 2001. Englsh translation summary of 2nd and 7th paragraphs attached.

* cited by examiner

METHOD FOR DIP COATING DOSAGE FORMS

CROSS REFERENCE TO RELATED APPLICATIONS

This is a continuation of prior U.S. application Ser. No. 10/122,999, filed Apr. 12, 2002, now abandoned which application claims the benefit of U.S. Application No. 60/291,127 filed on 15 May 2001 and U.S. Application No. 60/325,726 filed 28 Sep. 2001, which are all incorporated by reference in their entireties herein.

FIELD OF THE INVENTION

This invention relates to novel, water soluble, gelatin-free compositions for dip coating substrates, such as tablets and capsules, and methods for producing such dosage forms. This invention further relates to a method for increasing the weight gain of a water soluble, gelatin-free, film forming coating on a dip-coated tablet or caplet.

BACKGROUND OF THE INVENTION

During most of this century, hard gelatin capsules were a popular dosage form for prescription and over-the-counter (OTC) drugs. The ability to combine capsule halves having different colors provided manufacturers with a unique means of distinguishing various pharmaceutical products. Many patients preferred capsules over tablets, perceiving them as being easier to swallow. This consumer preference prompted pharmaceutical manufacturers to market certain products in capsule form even when they were also available in tablet form.

Generally, empty hard gelatin capsules are manufactured using automated equipment. This equipment employs rows of stainless steel pins, mounted on bars or plates, which are dipped into a gelatin solution maintained at a uniform temperature and fluidity. The pins are then withdrawn from the gelatin solution, rotated, and then inserted into drying kilns through which a strong blast of filtered air with controlled humidity is forced. A crude capsule half is thus formed over each pin during drying. Each capsule half is then stripped, trimmed to uniform length, filled and joined to an appropriate mating half.

An alternative to capsule products are caplets, which are solid, oblong tablets that are often coated with various polymers such as cellulose ethers to improve their aesthetics, stability, and swallowability. Typically, such polymers are applied to the tablets either from solution in organic solvents, or from aqueous dispersion via spraying. However, such spray-coated tablets lack the shiny surface and elegance of the hard gelatin capsules. Additionally, it is not commercially feasible to spray-coat a tablet with a different color coating on each end.

Another alternative to capsule products are "gelcaps," which are elegant, shiny, consumer-preferred dosage forms that are prepared by dipping each half of an elongated tablet in two different colors of gelatin solution. See U.S. Pat. Nos. 4,820,524; 5,538,125; 5,685,589; 5,770,225; 5,198,227; and 5,296,233, which are all incorporated by reference herein. A similar dosage form, commercially available as a "geltab", is prepared by dipping each half of a round, convex tablet into different colors of gelatin solution, as described in U.S. Pat. No. 5,228,916, U.S. Pat. No. 5,436,026 and U.S. Pat. No. 5,679,406, which are all incorporated by reference herein. As used herein, such "gelcaps" and "geltabs" shall be included within the broader term, "tablets."

However, the use of gelatin as a pharmaceutical coating material presents certain disadvantages and limitations, including the potential for decreased dissolution rate after extended storage due to cross-linking of the gelatin, potential for microbial contamination of the gelatin solution during processing, and long processing times due to extensive drying requirements. Further, the energy-related costs associated with gelatin coatings tend to be high since the gelatin material is typically applied to the substrates at an elevated temperature of at least about 40° C. in order to maintain fluidity of the gelatin, while the substrates are maintained at about 50° C. in order to minimize microbial growth.

Various attempts have been made to produce gelatin-free hard shell capsules. For example, WO 00/18835 discloses the combination of starch ethers or oxidized starch and hydrocolloids for use in preparing hard capsule shells via conventional dip molding processing. See also U.S. Pat. No. 4,001,211 (capsules prepared via pin dip coating with thermogelled methylcellulose ether compositions). However, due to potential tampering concerns, hard gelatin capsules are no longer a preferred delivery system for consumer (over-the-counter) pharmaceuticals, dietary supplements, or other such products. Additionally, the properties of an ideal composition into which steel pins are to be dipped then dried to form hard capsule shells thereon are not necessarily the same as those for dipping tablets to form a coating thereon. For example, relevant physical properties such as viscosity weight-gain, film thickness, tensile strength, elasticity, and moisture content will differ between compositions for hard capsule formation and for coating tablets. See e.g., U.S. Pat. No. 1,787,777 (Optimal temperatures of the substrate and coating solution, residence times in the solution, and drying conditions differ.)

One disadvantage associated with dipping tablets or capsules into a non-gelatin coating system is that the resulting coatings often lack adequate tensile strength, plasticity, hardness, and thickness. Moreover, the inclusion of plasticizers into such non-gelatin coating systems often results in tablets having soft, tacky coatings without a hardness sufficient to maintain their shape or smoothness during handling. In addition, many non-gelatin compositions do not adhere to the tablet substrate in an amount sufficient to uniformly cover the tablet after a single dipping. Further, many non-gelatin compositions lack the sufficient rheological properties necessary to maintain uniform color dispersion throughout the dipping and drying process. Although attempts have been made to improve the rheological properties of these compositions by, for example, increasing their solids content in order to increase viscosity. However, such compositions often disadvantageously resulted in undesirable coating aesthetics such as surface roughness, decreased gloss, and non-uniform coating thickness.

It is desirable to find a dip coating material, which not only produces a similar elegant, shiny, high gloss, consumer-preferred dosage form similar to that of gelatin-coated forms, but which is absent the limitations of gelatin, particularly those noted above.

SUMMARY OF THE INVENTION

The present invention provides for a film forming composition for dip coating a substrate comprising, consisting of, and/or consisting essentially of:
  a) hydroxypropylmethyl cellulose; and
  b) a thickener selected from the group consisting of xanthan gum, carrageenan, and mixtures thereof, wherein the composition possesses a surface gloss of at least 150 when applied via dip coating to a substrate.

Another embodiment of the present invention is directed to a water soluble composition for dip-coating a substrate comprising, consisting of, and/or consisting essentially of:
a) hydroxypropylmethyl cellulose; and
b) castor oil, wherein the composition possesses a surface gloss of at least 150 when applied via dip coating to a substrate.

Another embodiment of the present invention is directed to a water soluble composition for dip-coating a substrate comprising, consisting of, and/or consisting essentially of:
a) hydroxypropylmethyl cellulose; and
b) maltodextrin, wherein the composition possesses a surface gloss of at least 150 when applied via dip coating to a substrate.

We have found that when a dosage form is coated with the composition of the present invention, the result is an elegant, shiny, high gloss, consumer-preferred dosage form similar to that of a gelatin-coated form, but which lacks the limitations associated with gelatin, particularly those noted above. We have also found that when such a composition is used in dip coating and spray coating operations, it does not inhibit the dissolution of the active coated therewith. Further, we have found that the color uniformity of dosage forms coated with such compositions is improved upon the addition of a weight gain enhancer thereto.

DETAILED DESCRIPTION OF THE INVENTION

As used herein, "capsules" refer to hard shell compartments that enclose a dosable ingredient. "Tablets," as used herein, refer to compressed or molded solid dosage forms of any shape or size. "Caplets," as used herein, refer to solid, oblong-shaped tablets. "Gelcaps" refer to solid caplets having a glossy gelatinous coating, and "geltabs" refer to solid tablets having flat sides, convex opposing faces, and a glossy gelatinous coating. "Hardness" as used herein in connection with films or coatings indicates the resistance of the film/coating to deformation upon impact. "Water soluble," as used herein in connection with non-polymeric materials, shall mean from sparingly soluble to very soluble, i.e., not more than 100 parts water required to dissolve 1 part of the non-polymeric, water soluble solute. See Remington, "The Science and Practice of Pharmacy," pages 208-209 (2000). "Water soluble," as used herein in connection with polymeric materials, shall mean that the polymer swells in water and can be dispersed at the molecular level to form a homogeneous dispersion or colloidal "solution." "Surface gloss" as used herein, shall refer to amount of light reflectance as measured at a 60 degree incident angle using the method set forth in Example 7 herein.

Dimethicone is a well known pharmaceutical material consisting of linear siloxane polymers containing repeating units of the formula $\{—(CH_2)_2SiO\}_n$ stabilized with trimethylsiloxy end blocking units of the formula $[(CH_3)_3SiO—]$. Simethicone is the mixture of dimethicone and silicon dioxide. For the purposes of this invention, the two materials may be used interchangably.

The first embodiment of this invention is directed to water soluble, substantially gelatin-free, film forming compositions for dip coating tablets or manufacturing capsules via a dip molding process. One composition comprises, consists of, and/or consists essentially of a film former such as a cellulose ether, e.g., hydroxypropylmethylcellulose; and a thickener, such as a hydrocolloid, e.g., xanthan gum or carrageenan. In another embodiment, the composition comprises, consists of, and/or consists essentially of a film former such as a modified starch selected from waxy maize starch, tapioca dextrin, and derivatives and mixtures thereof; a thickener selected from sucrose, dextrose, fructose, maltodextrin, polydextrose, and derivatives and mixtures thereof; and a plasticizer, e.g., polyethylene glycol, propylene glycol, vegetable oils such as castor oil, glycerin, and mixtures thereof. In yet another embodiment, the composition comprises, consists of, and/or consists essentially of a film former such as a cellulose ether, e.g., hydroxypropylmethylcellulose; and optionally a plasticizer, such as vegetable oils, e.g., castor oil; and may optionally be substantially free of thickeners such as hydrocolloids, e.g. xanthan gum. In yet another embodiment, the composition comprises, consists of, and/or consists essentially of a film former such as a cellulose ether. e.g., hydroxypropylmethylcellulose; an extender, such as polycarbohydrates, e.g. maltodextrin; and optionally a plasticizer, such as glycols, e.g., polyethylene glycol; and may optionally be substantially free of thickeners such as hydrocolloids, e.g. xanthan gum. As used herein, "substantially gelatin-free" shall mean less than about 1 percent, e.g. less than about 0.5 percent, of gelatin in the composition, and "substantially free of thickeners" shall mean less than about 1 percent, e.g. less than about 0.01 percent, of thickeners in the composition.

Any film former known in the art is suitable for use in film forming composition of the present invention. Examples of suitable film formers include, but are not limited to, polyvinylalcohol (PVA), hydroxypropyl starch, hydroxyethyl starch, pullulan, methylethyl starch, carboxymethyl starch, methylcellulose, hydroxypropylcellulose (HPC), hydroxyethylmethylcellulose (HEMC), hydroxypropylmethylcellulose (HPMC), hydroxybutylmethylcellulose (HBMC), hydroxyethylethylcellulose (HEEC), hydroxyethylhydroxypropylmethyl cellulose (HEMPMC), pre-gelatinized starches, and polymers and derivatives and mixtures thereof.

One suitable hydroxypropylmethylcellulose compound is "HPMC 2910", which is a cellulose ether having a degree of substitution of about 1.9 and a hydroxypropyl molar substitution of 0.23, and containing, based upon the total weight of the compound, from about 29% to about 30% methoxyl and from about 7% to about 12% hydroxylpropyl groups. HPMC 2910 is commercially available from the Dow Chemical Company under the tradename, "Methocel E." "Methocel E5," which is one grade of HPMC-2910 suitable for use in the present invention, has a viscosity of about 4 to 6 cps (4 to 6 millipascal-seconds) at 20° C. in a 2% aqueous solution as determined by a Ubbelohde viscometer. Similarly, "Methocel E6," which is another grade of HPMC-2910 suitable for use in the present invention, has a viscosity of about 5 to 7 cps (5 to 7 millipascal-seconds) at 20° C. in a 2% aqueous solution as determined by a Ubbelohde viscometer. "Methocel E15," which is another grade of HPMC-2910 suitable for use in the present invention, has a viscosity of about 15000 cps (15 millipascal-seconds) at 20° C. in a 2% aqueous solution as determined by a Ubbelohde viscometer. As used herein, "degree of substitution" shall mean the average number of substituent groups attached to a anhydroglucose ring, and "hydroxypropyl molar substitution" shall mean the number of moles of hydroxypropyl per mole anhydroglucose.

As used herein, "modified starches" include starches that have been modified by crosslinking, chemically modified for improved stability, or physically modified for improved solubility properties. As used herein, "pro-gelatinized starches" or "instantized starches" refers to modified starches that have been pre-weated, then dried to enhance their cold-water solubility. Suitable modified starches are commercially available from several suppliers such as, for example, A.E. Staley Manufacturing Company, and National Starch & Chemical Company. One suitable modified starch includes the pregelatinized waxy maize derivative starches that are commercially available from National Starch & Chemical Company under the tradenames, "Purity Gum" and "FilmSet", and derivatives, copolymers, and mixtures thereof. Such waxy maize starches typically contain, based upon the total weight of the starch, from about 0 percent to about 18 percent of amylose and from about 100 percent to about 88 percent of amylopectin.

Suitable tapioca dextrins include those available from National Starch & Chemical Company under the tradename, "Crystal Gum" or "K-4484," and derivatives thereof such as modified food starch derived from tapioca, which is available from National Starch and Chemical under the tradename, "Purity Gum 40," and copolymers and mixtures thereof.

Any thickener known in the art is suitable for use in the film forming composition of the present invention. Examples of such thickeners include but are not limited to hydrocolloids such as alginates, agar, guar gum, locust bean, carrageenan, tara, gum arabic, tragacanth, pectin, xanthan, gellan, maltodextrin, galactomannan, pusstulan, laminarin, sderoglucan, gum arabic, inulin, pectin, whelan, rhamsan, zooglan, methylan, chitin, cyclodextrin, chitosan, and derivatives and mixtures thereof. Additional suitable thickeners include sucrose, dextrose, fructose, maltodextrin, polydextrose, and the like, and derivatives and combinations thereof.

Suitable xanthan gums include those available from C.P. Kelco Company under the tradename, "Keltrol 1000," "Xantrol 180," or "K9B310."

Any plasticizer known in the pharmaceutical art is suitable for use in the present invention, and may include, but not be limited to polyethylene glycol; glycerin; sorbitol; triethyl citrate; tribuyl citrate; dibutyl sebecate; vegetable oils such as castor oil; surfactants such as polysorbates, sodium lauryl sulfates, and dioctyl-sodium sulfosuccinates; propylene glycol; mono acetate of glycerol; diacetate of glycerol; triacetate of glycerol; natural gums and mixtures thereof. In solutions containing a cellulose ether film former, an optional plasticizer may be present in an amount, based upon the total weight of the solution, from about 0 percent to about 40 percent.

In one embodiment, the film forming composition for dip coating substrates may be substantially free of gelatin, i.e., e.g. contains less than about 1%, or less than about 0.01% of gelatin.

In another embodiment, the film forming composition for dip coating substrates may be substantially free of bovine derived materials, i.e., e.g. contains less than about 1%, or less than about 0.01% of bovine derived materials.

In embodiments wherein a cellulose ether film former is used in the composition, the film forming composition for dip coating substrates may be substantially free of hydrocolloids, i.e., e.g., contains less than about 1%, or less than about 0.01% of hydrocolloids.

In yet another embodiment, the film forming composition for dip coating substrates may be substantially free of plasticizers, i.e., e.g. contains less than about 1%, or less than about 0.01% of plasticizers.

In one embodiment, the film forming composition for dip coating substrates contains, based upon the total dry solids weight of the composition, from about 95 percent to less than about 100 percent, e.g. from about 95 percent to about 99.5 percent, of a film former such as a cellulose ether, e.g., hydroxypropylmethylcellulose; and from about 0.5 percent to about 5 percent of a thickener such as a hydrocolloid, e.g., xanthan gum.

In another embodiment, the film forming composition for dip coating substrates contains, based upon the total dry solids weight of the composition, from about 40 percent to about 60 percent, e.g. from about 50 percent to about 55 percent of a modified starch, e.g. a waxy maize starch, a tapioca dextrin, and/or mixtures and derivatives thereof; from about 15 percent to about 30 percent, e.g., from about 20 percent to about 25 percent of a plasticizer, e.g., glycerin, polyethylene glycol, propylene glycol, castor oil, and mixtures thereof; and from about 5 percent to about 25 percent, e.g., from about 10 percent to about 20 percent, of a thickener, e.g., sucrose, dextrose, fructose, maltodextrin, polydextrose, and mixtures thereof.

In yet another embodiment, the film forming composition for dip coating substrates contains, based upon the total dry solids weight of the composition, from about 95 percent to about 100 percent e.g. from about 97 percent to about 100 percent, of a film former such as a cellulose ether, e.g., hydroxypropylmethylcellulose.

In yet another embodiment, the film forming composition for dip coating substrates contains, based upon the total dry solids weight of the composition, from about 95 percent to about 100 percent, e.g. from about 97 percent to about 100 percent, of a film former such as a cellulose ether, e.g., hydroxypropylmethylcellulose, and is substantially free of hydrocolloids, i.e., e.g. contains less than about 1%, or less than about 0.01% of hydrocolloids.

In yet another embodiment the film forming composition for dip coating substrates contains, based upon the total dry solids weight of the composition, from about 95 percent to about 100 percent, e.g. from about 97 percent to about 100 percent, of a film former such as a cellulose ether, e.g., hydroxypropylmethylcellulose; and from about 0.1 percent to about 1.0 percent, e.g. from about 0.25 percent to about 0.5 percent of a plasticizer such as vegetable oils, e.g. Castor Oils.

In yet another embodiment, the film forming composition for dip coating substrates contains, based upon the total dry solids weight of the composition, from about 5 percent to about 99 percent, e.g. from about 50 percent to about 90 percent, or from about 80 percent to about 90 percent of a film former such as a cellulose ether, e.g., hydroxypropylmethylcellulose; from about 1 percent to about 80 percent, e.g. from about 5 percent to about 50 percent or from about 5 percent to about 40 percent of an extender, such as polycarbohydrates, e.g. maltodextrin; and from about 0.1 percent to about 20 percent, e.g. from about 2.5 percent to about 15 percent of a plasticizer such as glycols, e.g. polyethylene glycol. Examples of suitable dry compositions are disclosed in, for example, U.S. Pat. Nos. 5,470,581 and 5,183,808, which are incorporated by reference herein.

These film forming compositions are typically in the form of a dispersion for ease of dip coating substrates therein. Such dispersions contain a solvent in an amount, based upon the total weight of the dispersion, from about 30 percent to about 97 percent, for example, from about 80 percent to about 92 percent or from about 40 percent to about 75 percent. Examples of suitable solvents include, but are not limited to water; alcohols such as methanol, ethanol, and isopropanol, organic solvents such as methylene chloride, acetone, and the like; and mixtures thereof. In one embodiment, the solvent is water. The resulting film forming dispersion typically possesses a solids level of, based upon the total weight of the film forming dispersion, from about 3 percent to about 70 percent, for example from about 8 percent to about 20 percent or from about 25 percent to about 60 percent.

In one embodiment, the film forming composition for dip coating substrates contains, based upon the total wet weight of the dipping dispersion composition, from about 5 percent to about 20 percent, e.g. from about 8 percent to about 15 percent or from about 10 percent to about 14 percent, of a film former such as hydroxypropylmethylcellulose and from about 0.05 percent to about 0.2 percent, e.g. from about 0.08 percent to about 0.16 percent or from about 0.1 percent to about 0.14 percent, of a thickener such as xanthan gum.

In another embodiment, the film forming composition for dip coating substrates contains, based upon the total wet weight of the dipping dispersion composition, from about 20 percent to about 35 percent, e.g. from about 25 percent to about 30 percent, of a film former such as waxy maize starch, tapioca dextrin, and/or derivatives and mixtures thereof; from about 5 percent to about 20 percent, e.g., from about 10 percent to about 15 percent of a plasticizer such as glycerin, polyethylene glycol, propylene glycol, castor oil, and mixtures thereof; and from about 5 percent to about 15 percent of a thickener selected from sucrose, fructose, dextrose, maltodextrin, polydextrose, and mixtures thereof.

In yet another embodiment, the film forming composition for dip coating substrates contains, based upon the total wet weight of the dipping dispersion composition, from about 5 percent to about 25 percent, e.g. from about 8 percent to about 20 percent or from about 10 to about 16 percent, of a film former such as a cellulose ether, e.g., hydroxypropylmethylcellulose.

In yet another embodiment, the film forming composition for dip coating substrates contains, based upon the total wet weight of the dipping dispersion composition, from about 5 percent to about 25 percent, e.g. from about 8 percent to about 20 percent or from about 10 to about 16 percent, of a film former such as a cellulose ether, e.g., hydroxypropylmethylcellulose, and is substantially free of hydrocolloids, i.e., e.g. contains less than about 1%, or less than about 0.01% of hydrocolloids.

In yet another embodiment, the film forming composition for dip coating substrates contains, based upon the total wet weight of the dipping dispersion composition, from about 5 percent to about 25 percent, e.g. from about 8 percent to about 20 percent or from about 10 to about 16 percent, of a film former such as a cellulose ether, e.g., hydroxypropylmethylcellulose; and from about 0.001 percent to about 0.1 percent, e.g. from about 0.01 percent to about 0.09 percent of a plasticizer such as vegetable oils, e.g. castor oil.

In yet another embodiment, the film forming composition for dip coating substrates contains, based upon the total wet weight of the dipping dispersion composition, from about 1 percent to about 21 percent, e.g. from about 10 percent to about 19 percent or from about 16 percent to about 19 percent, of a film former such as a cellulose ether, e.g., hydroxypropylmethylcellulose; from about 0.1 percent to about 17 percent, e.g. from about 1 percent to about 11 percent or from about 1 percent to about 8 percent of an extender, such as polycarbohydrates, e.g. maltodextrin; and from about 0.02 percent to about 4 percent, e.g. from about 0.5 percent to about 3 percent of a plasticizer such as glycols, e.g. polyethylene glycol.

Optionally, the composition for dipping may further comprise other ingredients such as, based upon the total weight of the dipping solution, from about 0 percent to about 2 percent preservatives such as methylparaben and propylparaben, from about 0 percent to about 14 percent opacifying agents such as titanium dioxide, and/or from about 0 percent to about 14 percent colorants. See *Remington's Practice of Pharmacy*, Martin & Cook. $17^{th}$ ed., pp. 1625-30, which is herein incorporated by reference.

Any coloring agent suitable for use in pharmaceutical applications may be used in the present invention and may include, but not be limited to azo dyes, quinopthalone dyes, triphenylmethane dyes, xanthene dyes, indigoid dyes, iron oxides, iron hydroxides, titanium dioxide, natural dyes, and mixtures thereof. More specifically, suitable colorants include, but are not limited to patent blue V, acid brilliant green BS, red 2G, azorubine, ponceau 4R, amaranth, D&C red 33, D+C red 22, D+C red 26, D+C red 28, D+C yellow 10, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, antyhocyanines, turmeric, cochineal extract, clorophyllin, canthaxanthin, caramel, betanin, and mixtures thereof.

In one embodiment, each end of the tablet or capsule may be coated with dip coatings of different colors to provide a distinctive appearance for specialty products. See U.S. Pat. No. 4,820,524, which is incorporated by reference herein.

In one embodiment, the pharmaceutical dosage form is comprised of a) a core containing an active ingredient; b) an optional first coating layer comprised of a subcoating that substantially covers the core; and c) a second coating layer on the surface of the first coating layer, the second coating layer comprised of the dip coating composition of the present invention. As used herein, "substantially covers" shall mean at least about 95 percent of the surface area of the core is covered by the subcoating.

In an alternate embodiment, a first active ingredient may be contained in the first coating layer, and the core may contain a second active ingredient and/or an additional amount of the first active ingredient. In yet another embodiment, the active ingredient may be contained in the first coating layer, and the core may be substantially free, i.e., less than about 1 percent, e.g. less than about 0.1 percent, of active ingredient.

The use of subcoatings is well known in the art and disclosed in, for example, U.S. Pat. No. 3,185,626, which is incorporated by reference herein. Any composition suitable for film-coating a tablet may be used as a subcoating according to the present invention. Examples of suitable subcoatings are disclosed in U.S. Pat. Nos. 4,683,266, 4,543,370, 4,643,894, 4,828,841, 4,725,441, 4,802,924, 5,630,871, and 6,274,162, which are all incorporated by reference herein. Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating may be comprised of, based upon the total weight of the subcoating, from about 2 percent to about 8 percent, e.g. from about 4 percent to about 6 percent of a water-soluble cellulose ether and from about 0.1 percent to about 1 percent, castor oil, as disclosed in detail in U.S. Pat. No. 5,658,589, which is incorporated by reference herein. In another embodiment, the subcoating may be comprised of, based upon the total weight of the subcoating, from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400.

The dried subcoating typically is present in an amount, based upon the dry weight of the core, from about 0 percent to about 5 percent. The dried dip coating layer typically is present in an amount, based upon the dry weight of the core and the optional subcoating, from about 1.5 percent to about 10 percent.

The average thickness of the dried dip coating layer typically is from about 40 to about 400 microns. However, one skilled in the art would readily appreciate without undue experimentation that the dip coating thickness may be varied in order to provide a smoother, easier to swallow, dosage form or to achieve a desired dissolution profile. Moreover, the thickness of dipped film coatings may vary at different locations on the substrate depending upon its shape. For example, the thickness of the coating at an edge or corner of a substrate may be as much as 50 percent to 70 percent less than the thickness of the coating at the center of a major face of the substrate. This difference can be minimized by, for example, use of a thicker subcoating, or use of dipping compositions that result in higher weight gains on the substrate.

In embodiments wherein a thicker dip coating is desired, we have found that an effective amount of a weight gain enhancer selected from the group consisting of simethicone, polysorbate 80 and mixtures thereof, may be added to a film forming composition comprised, consisting of, and/or consisting essentially of a film former and an optional thickener such as a hydrocolloid. The weight gain enhancer is used in an amount sufficient to increase the weight gain of the coating solution, e.g. by at least about 10 percent, by at least about 20%, or by at least about 30% on a substrate when dried. The percent weight gain increase is determined based upon the difference between the total weight of the coated substrate with the coating composition including the weight gain enhancer, and the total weight of an coated equivalent substrate, which has been coated under similar processing conditions with a coating composition that does not include an effective amount of weight gain enhancer.

In one embodiment, the film former is a cellulose ether such as HPMC, and the thickener is a hydrocolloid such as xanthan gum and the weight gain enhancer is simethicone.

A suitable film forming composition capable of achieving increased weight gain of dip coating on a substrate may contain, based upon the total dry weight of the film forming composition, from about 40 percent to about 99.9 percent, e.g. from about 95 percent to about 99.5 percent, or from about 40 percent to about 60 percent of a film former; from about 0 percent to about 60 percent, e.g. from about 0 percent to about 10 percent, or from about 0.5 percent to about 5 percent, or from about 10 percent to about 25 percent of a thickener; and from about 0.01 percent to about 0.25 percent, e.g. from about 0.03 percent to about 0.15 percent of a weight gain enhancer. When aesthetics of the final tablet are of particular concern, it is recommended to not use greater than about 0.25 percent of a weight gain enhancer. As shown above, the amount of thickener suitable for use in the composition will vary depending upon, for example, the particular thickener selected and the desired properties of the coating. For example, when xanthan gum is the thickener of choice, the amount of xanthan gum thickener may range, based upon the total dry weight of the film forming composition, from about 0.5 percent to about 5 percent.

The film forming compositions of the present invention may be prepared by combining the film former, the thickener, and any optional ingredients such as plasticizers, preservatives, colorants, opacifiers, the weight gain enhancer, or other ingredients with the solvent using a high shear mixer until homogeneous under ambient conditions. In embodiments wherein a waxy maize starch derivative is used as a film former, the mixture may be heated to a temperature of about 60° C. to about 90° C. for faster dispersion of the ingredients. Alternatively, the film former and thickener may be preblended as dry powders, followed by addition of the resulting powder blend to the water and optional weight gain enhancer with high speed mixing. In order to remove substantially all of the bubbles from the resulting mixture, the pressure may then be decreased to about 5 inches Hg while reducing the mixing speed in order to avoid creating a vortex therein. Any other additional optional ingredients may then be added thereto at constant mixing.

It has surprisingly been found that substrates may be dipped into such solutions of the present invention using the same equipment and similar range of process conditions as used for the production of dip molded, gelatin-coated tablets. For example, both tablets and hard capsules may be coated using the aqueous dispersions of the present invention via known gelatin-dipping process parameters and equipment. Details of such equipment and processing conditions are known in the art and are disclosed at, for example, U.S. Pat. No. 4,820,524, which is incorporated by reference herein. Advantageously, because the coating solutions of the present invention are fluid at room temperature and are less susceptible to microbial growth than gelatin compositions, the dip coating process may occur under ambient temperature and pressure conditions.

The tablets dip coated with the composition of the present invention may contain one or more active agents. The term "active agent" is used herein in a broad sense and may encompass any material that can be carried by or entrained in the system. For example, the active agent can be a pharmaceutical, nutraceutical, vitamin, dietary supplement, nutrient, herb, foodstuff, dyestuff, nutritional, mineral, supplement, or favoring agent or the like and combinations thereof.

The active agents useful herein can be selected from classes from those in the following therapeutic categories: ace-inhibitors; alkaloids: antacids; analgesics; anabolic agents; anti-anginal drugs: anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics: anti-migraine agents; antinauseants; antipsychotios; antistroke agents; antithyroid preparations; anabolic drugs; antiobesity agents; antiparasitics; antipsychotics; antipyretics; antispasmodics; antithrombotics; antitumor agents; antitussives; antiulcer agents; anti-uricemic agents; anxiolytic agents; appetite stimulants; appetite suppressants; beta-blocking agents; bronchodilators; cardiovascular agents; cerebral dilators; chelating agents; cholecystekinin antagonists, chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins, laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

Active agents that may be used in the invention include, but are not limited to: acetaminophen; acetic acid; acetylsalicylic acid, including its buffered forms; acrivastine; albuterol and its sulfate; alcohol; alkaline phosphatase; allantoin; aloe; aluminum acetate, carbonate, chlorohydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; bromopheniramine and its maleate; buspirone; caffeine; calamine; calcium carbonate, casinate and hydroxide; camphor; captopril; cascara sagrada; castor oil; cefaclor; cefadroxil; cephalexin; centrizine and its hydrochloride; cetirizine; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine; cinnamedrine hydrochloride; citalopram; citric acid; clarithromycin; clemastine and its fumarate; clonidine; clorfibrate; cocoa butter; cod liver oil; codeine and its fumarate and phosphate; cortisone acetate; ciprofloxacin HCl; cyanocobalamin; cyclizine hydrochloride; cyproheptadine; danthron; dexbromopheniramine maleate; dextromethorphan and its hydrohalides; diazepam; dibucaine; dichloralphenazone; diclofen and its alkali metal sales; diclofenac sodium; digoxin; dihydroergotamine and its hydrogenateslmesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitertrate; erythropoietin; eucalyptol; famotidine; fenoprofen and its metal salts; ferrous fumarate, gluconate and sulfate; fexofenadine; fluoxetine; folic acid; fosphenytoin; 5-fluorouracil (5-FU); fluoxetine; flurbiprofen; furosemide; gabapentan; gentamicin; gemfibrozil; glipizide; glycerine; glyceryl stearate; granisetron; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its mono- and dinitrates; isoxicam; ketamine; kaolin; ketoprofen, lactic acid; lanolin; lecithin; leuprolide acetate; lidocaine and its hydrochloride salt; lifinopril; liotrix; loperamide, loratadine; lovastatin; luteinizing hormore; LHRH (lutenizing hormone replacement hormone); magnesium carbonate, hydroxide, salicylate, and trisilicate; meclizine; mefenamic acid; meclofenamic acid; meclofenamate sodium; medroxyprogesterone acetate; methenamine mandelate; menthol; meperidine hydrochloride; metaproterenol sulfate; methscopolamine and its nitrates: methsergide and its maleate; methyl nicotinate; methyl salicylate; methyl cellulose; methsuximide; metoclopramide and its halides/hydrates; metronidazole; metoprotol tartrate; miconazole nitrate; mineral oil; minoxidil; morphine; naproxen and its alkali metal sodium salts; nifedipine; neomycin sulfate; niacin; niacinamide; nicotine; nirotinamide; nimesulide; nitroglycerine; nonoxynol-9; norethindrone and its acetate; nystatin; octoxynol, octoxynol-9; octyl dimethyl PABA; octyl methoxycinnamate; omega-3 polyunsaturated fatty acids; omeprazole; ondansetron and its hydrochloride; oxolinic acid; oxybenzone: oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine; phenytoin; pirmenol; piroxicam and its salts; polymicin B sulfate; potassium chloride and nitrate; prazepam; procalnamide hydrochloride; procaterol; promethazine and its hydrochloride; propoxyphene and its hydrochloride and napsylate; praemiracetin; pramoxine and its hydrochloride salt; prochiorperazine and its maleate; propanolol and its hydrochloride; promethazine and its hydrochloride; propanolol; pseudoephedrine and its sulfates and hydrochlorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline, terfenadine; thiethylperazine and its maleate; timolol and its maleate; thioperidone; tramadol; trimetrexate; triazolam; tretinoin; tetracycline hydrochloride; tolmetin; tolnaftate; triclosan; trimethobenzamide and its hydrochloride; tripelennamine and its hydrochloride, tripolidine hydrochloride; undecylenic acid; vancornycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Active agents may further include, but are not limited to food acids; insoluble metal and mineral hydroxides, carbonates, oxides, polycarbophils, and salts thereof; adsorbates of active drugs on a magnesium trisilicate base and on a magnesium aluminum silicate base, and mixtures thereof. Mixtures and pharmaceutically acceptable salts of these and other actives can be used.

In one embodiment, the dosage forms coated with the dip coatings of the present invention provided for immediate release of the active ingredient, i.e. the dissolution of the dosage form conformed to USP specifications for immediate release tablets containing the particular active ingredient employed. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999).

We have unexpectedly found that the coatings formed by dipping substrates into the compositions of the present invention possessed excellent properties comparable to those possessed by gelatin coatings, e.g. crack resistance, hardness, thickness, color uniformity, smoothness, and gloss. Typically, the coatings of the present invention possessed a surface gloss of greater than about 150, e.g. greater than about 190 or greater than about 210 when measured according to the method set forth in example 7 herein.

In addition, tablets dip coated with the compositions of the present invention were superior to tablets dip coated with conventional gelatin-based coatings in several important ways. First, tablets dip coated with the compositions of the present invention advantageously retained acceptable dissolution characteristics for the desired shelf-life and storage period at elevated temperature and humidity conditions. In particular, the cellulose-ether based compositions according to the present invention were also advantageously more resistant to microbial growth, which thereby enabled a longer shelf-life or use-life of the dipping solution as well as a reduction in manufacturing cost. Second, the sugar-thickened dipping dispersions according to the present invention beneficially employed a lower water content relative to that of gelatin-containing dispersions, which thereby enabled a shorter drying cycle time. Although the water content of the other dipping dispersions of the present invention may have been higher than that typically found in gelatin-based dipping solutions, the cellulose-ether based compositions of the present invention surprisingly required a shorter drying cycle time relative to that for gelatin-containing compositions. Third, the dried coatings comprised of the compositions of the present invention also surprisingly and advantageously contained fewer air bubbles relative to the amount present in dried, gelatin based dipping compositions. Fourth, unlike dip processing with gelatin-containing compositions, substrates may optionally be dipped in the solutions of the present invention at room temperature, which is economically more beneficial. Fifth, the dip coated compositions of the present invention possessed a higher degree of glossiness relative to similar coatings applied via spray coating methods known in the art. The dip coated compositions of the present invention also possessed a similar degree of glossiness relative to that possessed by gelatin-containing dip or enrobing coatings, which are currently viewed as the industry benchmark for high gloss coatings. See, e.g., U.S. Pat. No. 6,274,162 (Typical gloss readings for standard, commercially available gel-dipped or gelatin enrobed tablets range from about 200 to 240 gloss units, gloss readings for standard, commercially available sugarcoated medicaments range from 177 to 209 gloss units, and gloss readings for a new, high-gloss coating system range from about 148 to about 243 gloss units.).

We have further unexpectedly found that the addition of an effective amount of weight gain enhancer to a film forming composition comprised of film former and hydrocolloid not only significantly increased the resulting dry weight of the dip coating on a substrate, but it also improved the color uniformity of the coating.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Example 1

Preparation of Subcoating Dispersions

An aqueous dispersion containing the ingredients set forth in Table A was prepared by combining all of the ingredients in a beaker under ambient conditions.

TABLE A

Aqueous Dispersion Subcoating Composition

| Ingredient | Part * |
|---|---|
| HPMC (2910, 5 mPs) from Dow Chemical Company under the tradename, "Methocel E-5" | 20 |
| Castor oil | 1 |
| Water | 241.5 |
| Total Coating Solution | 262.5 |
| % solids in coating solution | 8% |

* expressed in terms of part by weight unless otherwise noted

Additional aqueous dispersions containing the ingredients in Table B were similarly prepared:

TABLE B

Aqueous Dispersion Subcoating Compositions

| Ingredient | Ex 1A** | Ex 1B | Ex 1C | Ex 1D | Ex 1E |
|---|---|---|---|---|---|
| HPMC 2910, 5 mPs | 20 | 40 | 40 | 28 | 28 |
| Castor oil | 1 | 0 | 0 | 0 | 0 |
| water | 212.3 | 566.67 | 566.67 | 566.67 | 566.67 |
| maltodextrin | 0 | 53 | 53 | 67 | 67 |
| PEG 400 | 0 | 7 | 7 | 5 | 5 |
| Hydroxyethylcellulose* | 0 | 0 | 0 | 0 | 0 |
| Total coating solution | 233.3 | 666.67 | 666.67 | 666.67 | 666.67 |
| Wt % solids in coating solution | 9% | 15% | 15 | 15 | 15 |

*Available from Aqualon, under the tradename, "Natrosol 250L"
**all values expressed in terms of parts by weight unless otherwise noted Additional aqueous dispersions containing the ingredients in Table C were similarly prepared:

TABLE C

Aqueous Dispersion Subcoating Compositions

| Ingredient | Ex 1F** | Ex 1G | Ex 1H |
|---|---|---|---|
| water | 566.67 | 566.67 | 690.4 |
| maltodextrin | 71 | 71 | 0 |
| Castor oil | 0 | 0 | 0.13 |
| HPMC (1910, 5 mPas) | 0 | 0 | 32.4 |
| PEG 400 | 5 | 5 | 0 |
| Hydroxyethylcellulose* | 24 | 24 | 0 |
| Total coating solution | 666.67 | 666.67 | 722.9 |
| Wt % solids in coating solution | 15% | 15% | 4.5% |

*Available from Aqualon, under the tradename, "Natrosol 250L"
**all values expressed in terms of parts by weight unless otherwise noted Example 2

Preparation of Subcoated Tablets

Compressed tablets were prepared in accordance with the procedure set forth in Example 1 of U.S. Pat. No. 5,658,589 ("'589 Patent"), which was incorporated by reference herein.

The dispersion of Example 1 was then applied onto the compressed tablets via spraying in accordance with the procedure set forth in the examples of the '589 patent. As shown in Table D below, the dried subcoated tablets possessed an average 2% to 4% weight gain relative to the weight of the subcoating-free tablets.

This process was repeated with additional compressed tablets, but with the substitution of each, respective subcoating dispersion produced in Example 1A to 1H for that of Example 1. The percentage weight gain of the dried subcoated tablets are set forth below in Table D:

TABLE D

% Weight Gain of Dried Subcoated Tablets

| Example Number | % Weight Gain |
| --- | --- |
| 1A | 2 |
| 1B | 2 |
| 1C | 4 |
| 1D | 2 |
| 1E | 4 |
| 1F | 2 |
| 1G | 4 |
| 1H | 4 |

Example 3

Preparation of HPMC Coated Tablets

Aqueous HPMC dipping solutions containing the ingredients set forth in Table E were prepared:

TABLE E

Composition of HPMC Dipping Solutions

| Ingredient | Ex 3A * (g) | Ex 3B (g) | Ex 3C (g) | Ex 3D (%) | Ex 3E (%) | Ex 3F (%) |
| --- | --- | --- | --- | --- | --- | --- |
| HPMC E5 | 32.5 | 0 | 32.5 | 10 | 11 | 14 |
| Water | 200 | 200 | 200 | 89.89 | 88.879 | 85.85 |
| HPMC (2910, 15 mPs) | 0 | 20 | 0 | 0 | 0 | 0 |
| Xanthan gum | 0 | 0 | 0 | 0.11 | 0.121 | 0.15 |
| PEG 400 | 0 | 0 | 8 | 0 | 0 | 0 |
| % (wt.) solids in dipping solution | 14 | 9 | 17 | 10.11 | 11.121 | 14.15 |

* all values expressed in terms of weight (g) unless otherwise noted

Example 3A

Preparation of Dipping Solution of Example 3A

HPMC was dispersed into 200 ml of deionized water at a temperature of 70° C. After adding about 1 wt % FD&C blue dye thereto, the solution was mixed until homogeneous. The solution was then cooled to a temperature of about 22° C.

Example 3B

Preparation of Dipping Solution of Example 3B

The procedure of Example 3A was repeated, but with substitution of HPMC (2910, 15 mPs) for the HPMC E5.

Example 3C

Preparation of Dipping Solution of Example 3C

HPMC was dispersed into 200 ml of deionized water at a temperature of 70° C. After adding the PEG 400 thereto, the solution was mixed until homogeneous. The solution was then cooled to a temperature of about 22° C.

Example 3D

Preparation of Dipping Solution of Example 3D

HPMC and xanthan gum were added to purified water at a temperature of 80° C. until the powder was dispersed. After discontinuing the heat, the solution was divided into two parts. 4.35 wt. % of a yellow color dispersion available from Colorcon, Inc. under the tradename, "Opatint Yellow DD-2115" was added to the first part and mixed at a low speed until dispersed. 5.8% of a green color dispersion available from Colorcon, Inc. under the tradename, "Opatint Green DD-11000" was added to the second part and mixed at a low speed until dispersed. The two dispersed solutions were then stored under ambient conditions for about 12 hours.

Example 3E

Preparation of Dipping Solution of Example 3E

The procedure of Example 3D was repeated, but using the components of Example 3E Example 3F Preparation of Dipping Solution of Example 3F The procedure of Example 3D was repeated, but using the components of Example 3F.

Example 3G

Preparation of Hand-Dipped Dip Coated Tablets

The subcoated tablets prepared in accordance with Example 2 using the subcoating produced in Example 1H were hand-dipped into the dipping solutions of Example 3A for a dwell time of 1 second, removed from the dipping solution, then dried under ambient conditions.

This procedure was repeated, but with substitution of the dipping solutions of Examples 3B and 3C, respectively, for the dipping solution of Example 3A.

An observation of the resulting coatings showed the following:

Tablets Coated with Coating of Ex. 3A: The coatings were smooth, hard, and shiny, and had no bubbles or cracking. However, the coatings were non-uniform and thin, with land areas not well-covered. Upon exposure to ambient conditions for a six month period, no cracks were seen in the coatings.

Tablets Coated with Coating of Ex. 3B: The coating were shiny, with few bubbles and no cracking. The coatings were more uniform and rough relative to those of Example 3A. The coatings were also somewhat tacky and thin, with land areas not well-covered. Upon exposure to ambient conditions for a six month period, no cracks were seen in the coatings.

Tablets Coated with Coating of Ex. 3C: The coatings were shiny with few bubbles and no cracking. The coatings were more uniform and rough relative to those of Example 3A. The coatings were also somewhat tacky and thin, with land areas not well-covered. Upon exposure to ambient conditions for a six month period, no cracks were seen in the coatings.

Example 3H

Preparation of Production Scale Dipped Tablets

Additional subcoated tablets prepared in accordance with Example 2 using the subcoating produced in Example 1H were coated with the resulting dipping solution of Examples 3D using a commercial grade gel-dipping machine in accordance with the procedure described in U.S. Pat. No. 4,820,524, which is incorporated by reference herein.

This procedure was repeated, but with substitution of the dipping solutions of Examples 3E and 3F, respectively, for the dipping solution of Example 3D.

The average percentage weight gain of the dried dipped coatings were as set forth in Table F:

TABLE F

Weight Gain of Dried Dip Coating

| Example | % Wt. Gain of Dried Coating* |
| --- | --- |
| Ex. 3D | 0.75-2.26 |
| Ex. 3E | 1.9-3.52 |
| Ex. 3F | 3.2-5.8 |

*Relative to weight of dried subcoating and core

This example showed that the addition of xanthan gum to the HPMC dipping solution provided a viscosity enhancement to the dip coating, and thus an increased weight gain of the dip coating on the tablets.

Example 3I

Preparation of Dipping Solution of Example 3I

The procedure of Example 3D was repeated, but using the components of Example 3I, as set forth in Table M:

TABLE M

Composition of HPMC Dipping Solutions

| Ingredient | Ex 3I*(g) | Ex 3J (g) |
| --- | --- | --- |
| HPMC E5 | 14 | 12 |
| Water | 85.89 | 87.88 |
| HPMC (2910, 15 mPs) | 0 | 0 |
| Xanthan gum | 0.11 | 0.12 |
| PEG 400 | 0 | 0 |
| % (wt.) solids in dipping solution | 14.11 | 12.12 |

*all values expressed in terms of weight (g) unless otherwise noted

Example 3J

Preparation of Dipping Solution of Example 3J

The procedure of Example 3D was repeated, but using the components of Example 3J, as set forth in Table M above.

Example 4

Preparation of Pre-gelatinized Starch-Containing Dip Coating Solutions

Dipping solutions comprised of the components set forth in Table G were prepared by dispersing 75 g of the modified waxy maize starch into 200 ml of water under ambient conditions with mixing:

TABLE G

Pre-gelatinized starch-containing Dipping solutions

| Component/Other | Example 4A* | Example 4B |
| --- | --- | --- |
| Modified waxy maize starch (Purity ® Gum 59) | 75 | 125 |
| water | 200 | 200 |
| Total weight of solution | 275 | 325 |
| Wt % solids in dipping solution | 27 | 39 |

*all values expressed in terms of weight (g) unless otherwise noted

Dipping solutions comprised of the components set forth in Table H below were prepared by dispersing all of the components into 200 ml of water under ambient conditions with mixing until the resulting solution was clear

TABLE H

Pre-gelatinized starch-containing Dipping solutions With Simethicone of Example 4C

| Component | Tradename | Supplier | Amount used * |
| --- | --- | --- | --- |
| Modified waxy maize starch | Purity ® Gum 59 | National Starch & Chemical Co. | 125 |
| Simethicone | Antifoam ® | | 2 |
| Colloidal silicone dioxide | Aerosil ® A200 | | 6 |
| Glycerin | — | — | 63.5 |
| Sucrose | — | — | 38 |
| colorant | Opatint ® | | 6.9 |
| water | — | — | 200 |
| Total solids | | | 241.4 |
| TOTAL solution (w/ 55% solids) | | | 441.1 |

* all values expressed in terms of weight (mg) unless otherwise noted

Each side of the subcoated tablets prepared in accordance with Example 2 using the subcoating produced in Example 1H were hand-dipped into the dipping solution of Example 4A for a dwell time of about 1 second, pulled up, then dried under ambient conditions.

This procedure was repeated, but with substitution of the dipping solution of Example 4B for the dipping solution of Example 4A and with about a 3 day period between the completion of production of the dipping solution and the commencement of dip coating process.

This procedure was further repeated, but with substitution of the dipping solutions of Example 4C for the dipping solution of Example 4A and with about a 12 hour period between the completion of production of the dipping solution and the commencement of dip coating process.

An observation of the resulting coatings showed the following:

Tablets Coated with Dipping Solution of Ex. 4A: The coatings were very shiny, hard, smooth, even, and not tacky or cracked. However, the coatings were too thin, and land areas were not covered. No cracking after exposure to ambient conditions for a period of 6 months.

Tablets Coated with Dipping Solution of Ex. 4B: The coatings were smooth and shiny. Initially the land areas were covered; however, the coatings cracked after exposure to ambient conditions for a period of 6 months.

Tablets Coated with Dipping Solution of Ex. 4C: The coatings possessed excellent shine and cover, and were smooth with no cracks. No cracking after exposure to ambient conditions for a period of 2 months.

Example 5

Preparation of Pre-Gelatinized Starch-Containing Dip Coating Solutions

The procedure set forth in Example 4C is repeated, but without the inclusion of simethicone. Prior to coating the substrate, the solution is exposed to a vacuum pressure of 5 inches Hg in order to remove substantially all of the visible bubbles from the solution. The resulting coating possesses excellent shine and cover, and is smooth with no cracks.

Example 6

Effect of Simethicone on Coating Weight Gain

The following dip coating solutions set forth in Table I were prepared to illustrate the effect of simethicone as a weight gain enhancer. Amounts are percent based on the total weight of coating solution.

TABLE I

| | Dip Coating Solutions | | | | |
|---|---|---|---|---|---|
| Ingredient | 6A | 6B | 6C | 6D | 6E |
| HPMC 2910, 5 mPs | 12 | 12 | 12 | 12 | 12 |
| Xanthan Gum | 1 | 1 | 1 | 1 | 1 |
| Simethicone | 0 | 0.035 | 0.07 | 0.14 | 0.25 |
| Yellow color dispersion*** | 6 | 6 | 6 | 6 | 6 |
| Water | 81 | 80.965 | 80.93 | 80.86 | 80.75 |

***Yellow color dispersion was "Opatint" ® No. DD2125 obtained from Colorcon, Inc.

Dipping solutions A through E, above, were prepared in the following manner; Purified water was heated to about 35° C. HPMC and xanthan gum were added while mixing using a laboratory scale electric mixer (Janke and Kunkel, IKA Labortechnik, Staufen, Germany) with propeller blade at approximately 1000 rpm until the powders appeared uniformly dispersed. Heating was discontinued, and the resulting dispersion was allowed to stand overnight at room temperature. Simethicone and yellow color dispersion were then added with mixing at approximately 500 rpm.

Subcoated cores, prepared according to the method of example 1A, were pre-weighed, then dipped in solutions A, B, C, D, and E, above for a dwell time of about 2 seconds, pulled up, then dried at ambient conditions (about 22° C.). The cores were dipped simultaneously in sets of 7. Three separate sets of seven cores were dipped in each solution A through E. The average weight gain was determined from the triplicate sets of dipped cores from each coating solution.

Resulting weight gains were as follows in Table J:

TABLE J

| | Average Weight Gain | | | | |
|---|---|---|---|---|---|
| | Dipping Solution | | | | |
| | 6A | 6B | 6C | 6D | 6E |
| Average weight gain from dip coat (mg/tablet) | 13.3 | 20.8 | 22.3 | 23.7 | 19.1 |

Example 7

Surface Gloss Measurement of Coated Tablets

Tablets made according to the preceding examples were tested for surface gloss using an instrument available from TriCor Systems Inc. (Elgin, Ill.) under the tradename, "TriCor Model 805A/806H Surface Analysis System" and generally in accordance with the procedure described in "TriCor Systems WGLOSS 3.4 Model 805A/806H Surface Analysis System Reference Manual" (1996), which is incorporated by reference herein, except as modified below, This instrument utilized a COD camera detector, employed a flat diffuse light source, compared tablet samples to a reference standard, and determined average gloss values at a 60 degree incident angle. During its operation, the instrument generated a grey-scale image, wherein the occurrence of brighter pixels indicated the presence of more gloss at that given location.

The instrument also incorporated software that utilized a grouping method to quantity gloss, i.e., pixels with similar brightness were grouped together for averaging purposes.

The "percent full scale" or "percent ideal" setting (also referred to as the "percent sample group" setting), was specified by the user to designate the portion of the brightest pixels above the threshold that will be considered as one group and averaged within that group. "Threshold", as used herein, is defined as the maximum gloss value that will not be included in the average gloss value calculation. Thus, the background, or the non-glossy areas of a sample were excluded from the average gloss value calculations. The method disclosed in K. Fegley and C. Vesey, "The Effect of Tablet Shape on the Perception of High Gloss Film Coating Systems", which is available at www.colorcon.com as of 18 Mar. 2002 and incorporated by reference herein, was used in order to minimize the effects resulting from different tablet shapes, and thus report a metric that was comparable across the industry (Selected the 50% sample group setting as the setting which best approximated analogous data from tablet surface roughness measurements.).

After initially calibrating the instrument using a calibration reference plate (190-228; 294 degree standard; no mask, rotation 0, depth 0), a standard surface gloss measurement was then created using gel-coated caplets available from McNEIL-PPC, Inc. under the tradename, "Extra Strength Tylenol Gelcaps." The average gloss value for a sample of 112 of such gel-coated caplets was then determined, while employing the 25 mm full view mask (190-280), and configuring the instrument to the following settings:

Rotation: 0
Depth: 0.25 inches
Gloss Threshold: 95
% Full Scale: 50%
Index of Refraction: 1.57

The average surface gloss value for the reference standard was determined to be 269, using the 50% ideal (50% full scale) setting.

Samples of coated tablets prepared according to the preceding examples were then tested in accordance with the same procedure. The surface gloss values at the 50% ideal setting that were obtained are summarized in Table K below.

TABLE K

Gloss values of coated tablets

| | Example No. | | | | |
|---|---|---|---|---|---|
| | 3D | 3I | 3J | 4C | 6B |
| Type of coating | dipped | dipped | dipped | poured film plate | dipped |
| No. of tablets tested | 48 | 48 | 51 | | 3 |
| Gloss Value(% ideal at 50) | 234 | 247 | 229 | 259 | 221 |

Additional samples of other, commercially available gel coated tablets were also tested in accordance with the same procedure and compared to the same standard. The results are summarized in Table L below.

TABLE L

Gloss values of commercially available coated tablets

| Product | Motrin IB * Caplet (white) | Excedrin ** Aspirin free Caplets (red) | Excedrin ** Migraine Geltab (green side) | Excedrin ** Migraine Geltab (white side) | Extra Strength Tylenol Geltabs * (yellow side) | Extra Strength Tylenol Geltabs * (red side) |
|---|---|---|---|---|---|---|
| Type of coating | sprayed film | sprayed film | gelatin enrobed | gelatin enrobed | dipped | dipped |
| No. of tablets tested | 41 | 40 | 10 | 10 | 112 | 112 |
| Gloss Value(% ideal at 50) | 125 | 119 | 270 | 264 | 268 | 268 |

* Available from McNEIL-PPC, Inc.
** Available from Bristol-Myers, Squibb, Inc.

This Example showed that the tablets coated with the compositions of the present invention possessed a high surface gloss value that either was comparable to or exceeded that possessed by commercially—available gelatin coated tablets. In contrast, typical sprayed films possessed a substantially lower surface gloss, e.g. 119 to 125 in this Example.

Example 8

Preparation of Coated Tablets

Example 8A

Preparation of Tablets Spray Coated with Opadry® II Subcoating 122.8 kg (18% w/w) of a prepared blend containing HPMC 2910-6cP, maltodextrin, HPMC2910-3cP, HPMC2910-50cP, and PEG400 (commercially available from Colorcon Inc., West Point, Pa. as "Opadry® II") was added with mixing into 559.7 kg (82% w/w) of 35° C. purified water in a conventional pressure pot, and mixed with an air-driven propeller-type Lightnin mixer at a speed of 500 rpm. After the powder was completely added, the dispersion was mixed at 500 rpm for 2 hours, then allowed to stand without mixing at ambient conditions for 12 hours.

The resulting film coating dispersion was then applied onto compressed acetaminophen tablets, which were prepared in accordance with the procedure set forth in Example 1 of U.S. Pat. No. 5,658,589 ("'589 patent"), which is incorporated by reference herein, via spraying in accordance with the procedure set forth in the examples of the '589 patent. The resulting spray-coated tablets possessed a 4% weight gain relative to the weight of the uncoated tablet cores.

Examples 8B

Preparation of Tablets Spray Coated with HPMC/Castor Oil Subcoating 88.4 kg (9% w/w) of hydroxypropyl methylcellulose 2910, 5 mPs and 0.347 kg (0.04% w/w) of castor Oil were mixed into 593.8 kg (91% w/w) of purified water at 35° C. in a tank with mixer (Lee Industries) at a speed of 1750 rpm. After the powder was completely added, the mixer speed was increased to 3500 rpm for 15 minutes. The mixer speed was then reduced to 1750 rpm while the pressure was reduced to 15 inches of water for 2 hours to deaerate the dispersion.

The resulting film coating dispersion was then applied onto the compressed acetaminophen tablets of Example 8A via spraying in accordance with the procedure set forth above in Example 8A. The resulting spray coated tablets possessed a 4% weight gain relative to the weight of the uncoated tablet cores.

Example 8C

Preparation of Tablets Dip Coated with HPMC/Castor Oil Dipping Solutions

A dipping solution comprised of the components set forth in Table M below was produced:

TABLE M

HPMC/Castor Oil Clear Dipping Solutions

| | Example | | |
|---|---|---|---|
| | A&B | C&D | E&F |
| HPMC 2910 5 mPs | 9% | 13% | 13% |
| Castor Oil | 0.04% | 0.05% | 0.05% |
| Purified Water | 90.96% | 86.95% | 86.95% |

Purified water was heated to 80° C., then added to a Lee jacketed mix tank while mixing at a speed of 1750 rpm. After HPMC 2910, 5 mPs and castor oil were added thereto with mixing, the mixer speed was increased to 3500 rpm for 15 minutes. The mixer speed was then reduced to 1750 rpm while the temperature of the dispersion was reduced to 35° C. and the pressure was reduced to 15 inches water for deaeration. After mixing the dispersion for 2 hours, the resulting dispersion remained under constant pressure conditions for an additional 3 hours without mixing.

The colorant of Example 8C-a was then added to 96 kg of the resulting clear dipping solutions with mixing at a 1750 rpm speed in the amounts set forth in Table N below:

dance with Example 8C-a and 8C-b using a commercial grade gel-dipping machine and in accordance with the procedure described in U.S. Pat. No. 4,820,524, which is incorporated by reference herein, using the dipping solution temperatures reported in the table above. This procedure was independently repeated on subcoated tablets, which were prepared in accordance with the procedure set forth above in Example 8B, for each of the colored dipping solutions 8C-c through 8C-f in Table N above.

A visual comparison of the dip-coated tablets prepared according to examples 8C-a and 8C-b with those prepared in accordance with Examples 8C-c through 8C-f revealed that the former did not possess complete coating coverage around the edges of the tablets. By contrast, the dip-coated tablets prepared according to examples 8C-c through 8C-f possessed a superior good coating coverage around the tablet edges. This indicated that a weight gain of 16 mg per gelcap (such as that produced by the 9% HPMC formula of examples 8C-a and 8C-b) was insufficient for the HPMC/Castor Oil dipping formula, while a weight gain of 20 to 26 mg per gelcap/geltab (such as that produced by the 13% HPMC formula of examples 8C-c through 8C-f) provided good coverage.

In addition, a visual comparison of the HPMC/Castor Oil dip-coated tablets of Examples 8C-c through 8C-f and the HPMC/Xanthan Gum dip-coated tablets of Examples 3I and 3J indicated that the former possessed superior gloss and surface smoothness. The superior gloss and smoothness were likely attributed to the inclusion of castor oil in the dip coating.

Example 9

Preparation of Tablets Dip Coated with HPMC/Maltodextrin/PEG Dipping Solutions 143.3 kg (21% w/w) of the Opadry® II blend of Example 8A was added into 539.2 kg (79% w/w) of 35° C. purified water while mixing at a speed of 3500 rpm for 15 minutes.

TABLE N

HPMC/Castor Oil Colored Dipping Solutions

| | Example | | | | | |
|---|---|---|---|---|---|---|
| | 8C-a | 8C-b | 8C-c | 8C-d | 8C-e | 8C-f |
| Colorant | Opatint (DD-1761) | Opatint (DD-2125) | Opatint (DD-1761) | Opatint (DD-2125) | Opatint (DD-10516) | Opatint (DD-18000) |
| Amount of colorant (kg) | 2.700 | 2.570 | 2.700 | 2.570 | 4.072 | 2.175 |
| Color | red | yellow | red | yellow | blue | white |
| Visc/Temp | 490 cps @40 C. | 518 cps @40 C. | 612 cps @30 C. | 457 cps @30 C. | 351 cps @40 C. | 319 cps @40 C. |
| Dipping Temp | 40 C. | 40 C. | 30 C. | 30 C. | 40 C. | 40 C. |
| Weight Gain in dipping (mg/tablet) | 16* | 16* | 26** | 26** | 20*** | 20*** |
| Gloss | 229 | 229 | 249 | 228 | 238 | 233 |

*indicates total weight gain for a tablet having an 8Ca coating on one half and an 8Cb coating on the other
**indicates total weight gain for a tablet having an 8Cc coating on one half and an 8Cd coating on the other
***indicates total weight gain for a tablet having an 8Ce coating on one half and an 8Cf coating on the other This procedure was independently repeated for each of the colorants set forth above in Table N.

Subcoated tablets, which were prepared in accordance with the procedure set forth above in Example 8A, were dip-coated with the dip-coating solution prepared in accor- The mixer speed was then decreased to 1750 rpm, and the tank evacuated to 30 PSIA to deaerate the solution for 5 hours. 2.70 kg of Colorant (Opatint® Red DD-1761, from Colorcon Inc.) was then added to 96 kg of the clear dipping solution while mixing at a speed of 1750 rpm. 2.570 kg of Colorant (Opatint® Yellow DD-2125, from Colorcon Inc.) was then added to a second 96 kg portion of the clear dipping solution while mixing at a speed of 1750 rpm until dispersed.

Subcoated tablets, which were prepared in accordance with the procedure and materials set forth above in Example 8B, were dip-coated with the dip-coating solution prepared in accordance with this Example using a commercial grade gel-dipping machine and in accordance with the procedure described in U.S. Pat. No. 4,820,524, which is incorporated by reference herein, using a dipping solution temperature of 30° C. The viscosity of the dipping solutions was 607 cPs at 30° C. for the yellow solution, and 677 cPs at 30° C. for the red solution. An average weight gain of about 27 mg/gelcap was obtained.

Seventy-two (72) dipped gel caps produced in accordance with this Example were tested for surface gloss in accordance with the procedure set forth in Example 7. The average surface gloss for these dipped gelcaps was 258 gloss units.

Example 10

Preparation of Tablets Dip Coated with HPMC/Carrageenan Dipping Solutions 88.4 kg (13% w/w) of HPMC 2910-5 mPs, 0.347 kg of Castor Oil (0.05% w/w), and 0.68 kg (0.1% w/w) of kappa Carrageenan-911 were added into a tank containing 590 kg (87% w/w) of 80° C. purified water while mixing at a speed of 1750 rpm. After the addition was complete, the mixer speed was increased to 3500 rpm for 15 minutes. The mixer speed was then decreased to 1750 rpm, and the tank evacuated to 15 inches of water to deaerate the solution for 2 hours. Mixing was then stopped, and the dispersion was allowed to stand at constant pressure for an additional 3 hours. 2.175 kg of Colorant (Opatint® White OD-18000, from Colorcon Inc.) was then added to 96 kg of the clear dipping solution while mixing at a speed of 1750 rpm. 4.072 kg of Colorant (Opatint® Blue DD-10516, from Colorcon Inc.) was then added to a second 96 kg portion of the clear dipping solution while mixing at a speed of 1750 rpm until dispersed.

Subcoated tablets, which were prepared in accordance with the procedure and materials set forth above in Example 8B, were dip-coated with the dip-coating solution prepared in accordance with this Example using a commercial grade gel-dipping machine and in accordance with the procedure described in U.S. Pat. No. 4,820,524, which is incorporated by reference herein, using a dipping solution temperature of 40° C. An average weight gain of about 20 mg/gelcap was obtained.

Eighty-eight (88) dipped gel caps produced in accordance with this Example were tested for surface gloss in accordance with the procedure set forth in Example 7. The average surface gloss for these dipped geltabs was 232 gloss units.

We claim:

1. A method of producing a coated dosage form having a core and an outer coating on the surface of the coated dosage form, wherein the core comprises a pharmaceutical active ingredient and the outer coating comprises hydroxypropylmethyl cellulose and a thickener selected from the group consisting of xanthan gum, carrageenan, and mixtures thereof, the method comprising:

(i) dipping the core into a dipping solution; and
(ii) drying the dipped core of step (i);

wherein the coated dosage form is substantially free of gelatin.

2. The method of claim 1, wherein the outer coating is comprised of, based upon the total dry weight of the outer coating, (a) from about 40 percent to about 99.5 percent of hydroxypropylmethyl cellulose; and
(b) from about 0.5 percent to about 5 percent of the thickener.

3. The method of claim 2, wherein the thickener comprises xanthan gum.

4. The method of claim 3, wherein the outer coating further comprises, based upon the total dry weight of the outer coating, up to about 40 percent of a plasticizer.

5. The method of claim 4, wherein the plasticizer comprises propylene glycol.

6. The method of claim 5, wherein the outer coating further comprises, based upon the total dry weight of the composition, up to about 14 percent of a coloring agent.

7. The method of claim 3, wherein the outer coating further comprises, based upon the total dry weight of the composition, up to about 14 percent of a coloring agent.

8. The method of claim 1, wherein the thickener comprises xanthan gum.

9. The method of claim 1, wherein the outer coating further comprises, based upon the total dry weight of the outer coating, up to about 40 percent of a plasticizer.

10. The method of claim 9 wherein the plasticizer is selected from the group consisting of polyethylene glycol, glycerin, sorbitol, triethyl citrate, tribuyl citrate, dibutyl sebecate, vegetable oils, surfactants, propylene glycol, mono acetate of glycerol, diacetate of glycerol, triacetate of glycerol, natural gums, and mixtures thereof.

11. The method of claim 9, wherein the plasticizer comprises propylene glycol.

12. The method of claim 1, wherein the outer coating further comprises, based upon the total dry weight of the composition, up to about 14 percent of a coloring agent.

13. The method of claim 12, wherein the coloring agent is selected from the group consisting of azo dyes, quinopthalone dyes, triphenylmethane dyes, xanthene dyes, indigoid dyes, iron oxides, iron hydroxides, titanium dioxide, natural dyes, and mixtures thereof.

14. The method of claim 6, wherein the coloring agent is selected from the group consisting of azo dyes, quinopthalone dyes, triphenylmethane dyes, xanthene dyes, indigoid dyes, iron oxides, iron hydroxides, titanium dioxide, natural dyes, and mixtures thereof.

15. The method of claim 1, wherein the core is substantially covered with a subcoating prior to the dipping into the dipping solution.

16. The method of claim 15, wherein the subcoating comprises materials selected from the group consisting of cellulose ethers, plasticizers, polycarbohydrates, pigments, opacifiers, and mixtures thereof.

17. The method of claim 15 wherein the subcoating comprises materials selected from the group consisting of hydroxypropylmethylcellulose, castor oil, polyethylene glycol, polysorbate 80, maltodextrin, and mixtures thereof.

18. The method of claim 15, wherein the subcoating is comprised of, based upon the total dry weight of the coated dosage form,
(a) from about 2 percent to about 8 percent of a water-soluble cellulose ether selected from the group consisting of hydroxypropylmethylcellulose, hydroxypropylcellulose, hydroxyethylcellulose, and mixtures thereof;
(b) from about 0.1 percent to about 1 percent castor oil.

19. The method of claim 15, wherein the subcoating is comprised of, based upon the total dry weight of the coated dosage form,
(a) from about 4 percent to about 6 percent hydroxypropylmethylcellulose; and
(b) from about 0.1 percent to about 1 percent castor oil.

20. The method of claim 1, wherein the outer coating substantially covers the core.

21. The method of claim 1, wherein the coated dosage form meets USP dissolution requirements for immediate release forms of the pharmaceutical active ingredient.

22. A method of producing a coated dosage form having a core and an outer coating on the surface of the coated dosage form, wherein the core comprises a pharmaceutical active ingredient and the outer coating comprises hydroxypropylmethyl cellulose and a thickener selected from the group consisting of xanthan gum, carrageenan, and mixtures thereof, the method comprising:
(i) dipping the core into a dipping solution, wherein the dipping solution comprises the hydroxypropylmethyl cellulose and the thickener; and
(ii) drying the dipped core of step (i);
wherein the core is substantially covered with a subcoating prior to the dipping into the dipping solution, and wherein the subcoating is comprised of, based upon the total dry weight of the subcoating,
(a) from about 20 percent to about 50 percent hydroxypropylmethylcellulose;
(b) from about 45 percent to about 75 percent maltodextrin; and
(c) from about 1 percent to about 10 percent PEG 400.

23. The method of claim 22, wherein the subcoating is comprised of, based upon the total dry weight of the subcoating,
(a) from about 25 percent to about 40 percent hydroxyethylcellulose;
(b) from about 50 percent to about 70 percent maltodextrin;
(c) from about 5 percent to about 10 percent PEG 400.

24. A method of producing a coated dosage form having a core and an outer coating on the surface of the coated dosage form, wherein the core comprises a pharmaceutical active ingredient and the outer coating comprises hydroxypropylmethyl cellulose and a thickener selected from the group consisting of xanthan gum, carrageenan, and mixtures thereof, the method comprising:
(i) dipping the core into a dipping solution; and
(ii) drying the dipped core of step (i);
wherein the dipping solution comprises, based upon the total weight of the solution,
(a) from about 10 percent to about 14 percent of hydroxypropylmethylcellulose; and
(b) from about 0.1 percent to about 0.14 percent of xanthan gum.

25. A method of producing a coated dosage form having a core and an outer coating on the surface of the coated dosage form, wherein the core comprises a pharmaceutical active ingredient and the outer coating comprises hydroxypropylmethyl cellulose and a thickener selected from the group consisting of xanthan gum, carrageenan, and mixtures thereof, the method comprising:
(i) dipping the core into a dipping solution; and
(ii) drying the dipped core of step (i);
wherein the outer coating further comprises a weight gain enhancer selected from the group consisting of simethicone, polysorbate 80, and mixtures thereof.

26. A method of producing a coated dosage form having a core and an outer coating on the surface of the coated dosage form, wherein the core comprises a pharmaceutical active ingredient and the outer coating comprises hydroxypropylmethyl cellulose and a thickener selected from the group consisting of xanthan gum, carrageenan, and mixtures thereof, the method comprising:
(i) dipping the core into a dipping solution; and
(ii) drying the dipped core of step (i)
wherein the outer coating has a surface gloss of at least 150.

* * * * *